(12) United States Patent
Gonzalez-Hernandez (10) Patent No.: US 10,524,919 B2
(45) Date of Patent: Jan. 7, 2020

(54) SYSTEM AND METHOD FOR FRACTURE REPLACEMENT OF COMMINUTED BONE FRACTURES OR PORTIONS THEREOF ADJACENT BONE JOINTS

(71) Applicant: TOBY ORTHOPAEDICS, INC., Miami, FL (US)

(72) Inventor: Eduardo Gonzalez-Hernandez, Miami, FL (US)

(73) Assignee: TOBY ORTHOPAEDICS, INC., Miami, FL (US)

( * ) Notice: Subject to any disclaimer, the term of this patent is extended or adjusted under 35 U.S.C. 154(b) by 0 days.

(21) Appl. No.: 15/702,006

(22) Filed: Sep. 12, 2017

(65) Prior Publication Data

US 2018/0000600 A1    Jan. 4, 2018

Related U.S. Application Data

(62) Division of application No. 14/522,702, filed on Oct. 24, 2014, now Pat. No. 9,757,240, which is a division of application No. 13/282,810, filed on Oct. 27, 2011, now Pat. No. 8,870,963.

(60) Provisional application No. 61/407,072, filed on Oct. 27, 2010.

(51) Int. Cl.
    *A61F 2/38*     (2006.01)
    *A61B 17/80*    (2006.01)
    *A61F 2/40*     (2006.01)
    *A61F 2/30*     (2006.01)

(52) U.S. Cl.
    CPC ............ *A61F 2/3804* (2013.01); *A61B 17/80* (2013.01); *A61B 17/8061* (2013.01); *A61F 2/4003* (2013.01); *A61F 2/3859* (2013.01); *A61F 2/4014* (2013.01); *A61F 2002/30433* (2013.01);
    (Continued)

(58) Field of Classification Search
    CPC .. A61F 2/38; A61F 2/3804; A61F 2002/3822; A61F 2002/4014
    See application file for complete search history.

(56) References Cited

U.S. PATENT DOCUMENTS 1,950,799 A    3/1934    Jones
2,500,370 A    3/1950    McKibbin
2,555,291 A    5/1951    Poupitch
(Continued)

FOREIGN PATENT DOCUMENTS

DE    86 28 766 U1    12/1986
DE    89 07 443 U1    9/1989
(Continued)

OTHER PUBLICATIONS

ACUMED; ACU-LOC Wrist Plating System; Jul. 2009; 20 pages.
(Continued)

*Primary Examiner* — Bruce E Snow
(74) *Attorney, Agent, or Firm* — Martin & Ferraro, LLP (57) ABSTRACT

The system and method serves in facilitating replacement of comminuted bone fractures or portions thereof adjacent bone joints. The system and method employs a prosthesis to replace at least a portion of the comminuted bone fractures. The prosthesis serves in reproducing the articular surface of the portion or portions of the comminuted bone fractures that are replaced. In doing so, the prosthesis serves in restoring joint viability and corresponding articulation thereof.

16 Claims, 2 Drawing Sheets

(52) U.S. Cl.
CPC .............. *A61F 2002/30578* (2013.01); *A61F 2002/30616* (2013.01); *A61F 2002/3822* (2013.01)

(56) References Cited

U.S. PATENT DOCUMENTS

| | | |
|---|---|---|
| 2,580,821 A | 1/1952 | Toufick |
| 2,682,265 A | 6/1954 | Collison |
| 2,853,114 A | 9/1958 | Barry |
| 2,875,663 A | 3/1959 | Wieber |
| 3,489,143 A | 1/1970 | Halloran |
| 3,552,389 A | 1/1971 | Allgower et al. |
| 3,579,831 A | 5/1971 | Stevens et al. |
| 3,716,050 A | 2/1973 | Johnston |
| 3,791,380 A | 2/1974 | Dawidowski |
| 3,824,995 A | 7/1974 | Getscher |
| 3,900,025 A | 8/1975 | Barnes, Jr. |
| 4,029,091 A | 6/1977 | von Bezold |
| 4,263,904 A | 4/1981 | Judet |
| 4,535,768 A | 8/1985 | Hourahane et al. |
| 4,683,878 A | 8/1987 | Carter |
| 4,733,654 A | 3/1988 | Marino |
| 4,776,330 A | 10/1988 | Chapman et al. |
| 4,790,302 A | 12/1988 | Colwill et al. |
| 4,794,919 A | 1/1989 | Nilsson |
| 4,796,612 A | 1/1989 | Reese |
| 4,838,264 A | 6/1989 | Bremer et al. |
| 4,858,602 A | 8/1989 | Seidel et al. |
| 4,870,957 A | 10/1989 | Goble et al. |
| 5,003,969 A | 4/1991 | Azer et al. |
| 5,015,248 A | 5/1991 | Burstein et al. |
| 5,041,113 A | 8/1991 | Biedermann et al. |
| 5,041,114 A | 8/1991 | Chapman et al. |
| 5,180,383 A | 1/1993 | Haydon |
| 5,190,544 A | 3/1993 | Chapman et al. |
| 5,324,291 A | 6/1994 | Ries et al. |
| 5,356,410 A | 10/1994 | Pennig |
| 5,364,399 A | 11/1994 | Lowery et al. |
| 5,423,860 A | 6/1995 | Lizardi et al. |
| 5,437,667 A | 8/1995 | Papierski et al. |
| 5,443,516 A | 8/1995 | Albrektsson et al. |
| 5,458,654 A | 10/1995 | Tepic |
| 5,462,547 A | 10/1995 | Weigum |
| 5,472,444 A | 12/1995 | Huebner et al. |
| 5,505,734 A | 4/1996 | Caniggia et al. |
| 5,578,035 A | 11/1996 | Lin |
| 5,584,835 A | 12/1996 | Greenfield |
| 5,586,985 A | 12/1996 | Putnam et al. |
| 5,601,553 A | 2/1997 | Trebing et al. |
| 5,620,449 A | 4/1997 | Faccioli et al. |
| 5,658,287 A | 8/1997 | Hofmann et al. |
| 5,665,088 A | 9/1997 | Gil et al. |
| 5,674,222 A | 10/1997 | Berger et al. |
| 5,676,667 A | 10/1997 | Hausman |
| 5,681,311 A | 10/1997 | Foley et al. |
| 5,709,686 A | 1/1998 | Talos et al. |
| 5,725,593 A | 3/1998 | Caracciolo |
| 5,749,872 A | 5/1998 | Kyle et al. |
| 5,766,174 A | 6/1998 | Perry |
| 5,776,194 A | 7/1998 | Mikol et al. |
| 5,779,704 A | 7/1998 | Kim |
| 5,785,712 A | 7/1998 | Runciman et al. |
| 5,840,078 A | 11/1998 | Yerys |
| 5,868,749 A | 2/1999 | Reed |
| 5,931,839 A | 8/1999 | Medoff |
| 5,976,139 A | 11/1999 | Bramlet |
| 5,980,575 A | 11/1999 | Albrektsson et al. |
| 6,030,389 A | 2/2000 | Wagner et al. |
| 6,096,040 A | 8/2000 | Esser |
| 6,149,653 A | 11/2000 | Deslauriers |
| 6,152,927 A | 11/2000 | Farris et al. |
| 6,200,330 B1 | 3/2001 | Benderev et al. |
| 6,206,881 B1 | 3/2001 | Frigg et al. |
| D443,060 S | 5/2001 | Benirschke et al. |
| 6,270,499 B1 | 8/2001 | Leu et al. |
| D449,692 S | 10/2001 | Michelson |
| 6,302,887 B1 | 10/2001 | Spranza et al. |
| 6,331,179 B1 | 12/2001 | Freid et al. |
| 6,348,052 B1 | 2/2002 | Sammarco |
| 6,358,250 B1 | 3/2002 | Orbay |
| 6,364,881 B1 | 4/2002 | Apgar et al. |
| 6,364,882 B1 | 4/2002 | Orbay |
| 6,379,359 B1 | 4/2002 | Dahners |
| 6,398,783 B1 | 6/2002 | Michelson |
| 6,406,478 B1 | 6/2002 | Kuo |
| 6,409,768 B1 | 6/2002 | Tepic et al. |
| 6,413,259 B1 | 7/2002 | Lyons et al. |
| 6,440,135 B2 | 8/2002 | Orbay et al. |
| 6,468,278 B1 | 10/2002 | Muckter |
| 6,572,620 B1 | 6/2003 | Schon et al. |
| 6,620,195 B2 | 9/2003 | Goble et al. |
| 6,623,486 B1 | 9/2003 | Weaver et al. |
| 6,663,669 B1 | 12/2003 | Reiley |
| 6,669,701 B2 | 12/2003 | Steiner et al. |
| 6,695,844 B2 | 2/2004 | Bramlet et al. |
| 6,706,046 B2 | 3/2004 | Orbay et al. |
| 6,712,820 B2 | 3/2004 | Orbay |
| 6,719,759 B2 | 4/2004 | Wagner et al. |
| 6,730,090 B2 | 5/2004 | Orbay et al. |
| 6,776,781 B1 | 8/2004 | Uwaydah |
| 6,863,671 B1 | 3/2005 | Strobel et al. |
| 6,866,665 B2 | 3/2005 | Orbay |
| 6,916,323 B2 | 7/2005 | Kitchens |
| 6,945,973 B2 | 9/2005 | Bray |
| 7,001,388 B2 | 2/2006 | Orbay et al. |
| 7,063,701 B2 | 6/2006 | Michelson |
| 7,128,744 B2 | 10/2006 | Weaver et al. |
| D536,453 S | 2/2007 | Young et al. |
| 7,220,246 B2 | 5/2007 | Raulerson et al. |
| 7,229,444 B2 | 6/2007 | Boyd |
| 7,229,445 B2 | 6/2007 | Hayeck et al. |
| 7,235,079 B2 | 6/2007 | Jensen et al. |
| 7,354,441 B2 | 4/2008 | Frigg |
| 7,500,983 B1 | 3/2009 | Kaiser et al. |
| 7,563,263 B2 | 7/2009 | Orbay et al. |
| 7,582,107 B2 | 9/2009 | Trail et al. |
| 7,591,823 B2 | 9/2009 | Tipirneni |
| 7,604,657 B2 | 10/2009 | Orbay et al. |
| 7,637,908 B1 | 12/2009 | Gonzalez-Hernandez |
| 7,651,517 B2 | 1/2010 | Konieczynski et al. |
| 7,655,029 B2 | 2/2010 | Niederberger et al. |
| 7,695,472 B2 | 4/2010 | Young |
| 7,722,653 B2 | 5/2010 | Young et al. |
| 7,740,648 B2 | 6/2010 | Young et al. |
| 7,744,638 B2 | 6/2010 | Orbay |
| 7,776,076 B2 | 8/2010 | Grady, Jr. et al. |
| 7,780,667 B2 | 8/2010 | Watanabe et al. |
| 7,780,710 B2 | 8/2010 | Orbay et al. |
| 7,896,886 B2 | 3/2011 | Orbay et al. |
| 7,909,859 B2 | 3/2011 | Mosca et al. |
| 7,914,532 B2 | 3/2011 | Shaver et al. |
| 7,927,341 B2 | 4/2011 | Orbay et al. |
| 7,938,850 B2 | 5/2011 | Orbay et al. |
| 7,951,176 B2 | 5/2011 | Grady et al. |
| 7,951,178 B2 | 5/2011 | Jensen |
| 7,955,364 B2 | 6/2011 | Ziolo et al. |
| D643,121 S | 8/2011 | Milford et al. |
| 8,021,402 B2 | 9/2011 | Martin et al. |
| D646,785 S | 10/2011 | Milford |
| 8,062,296 B2 | 11/2011 | Orbay et al. |
| 8,062,367 B2 | 11/2011 | Kirschman |
| 8,100,953 B2 | 1/2012 | White et al. |
| 8,182,485 B1 | 5/2012 | Gonzalez-Hernandez |
| 8,317,842 B2 | 11/2012 | Graham et al. |
| 8,361,075 B2 | 1/2013 | Gonzalez-Hernandez |
| 8,469,999 B2 | 6/2013 | Gonzalez-Hernandez |
| 8,523,902 B2 | 9/2013 | Heaven et al. |
| 8,556,946 B2 | 10/2013 | Prandi |
| 8,574,234 B2 | 11/2013 | Gonzalez-Hernandez |
| 8,597,363 B2 | 12/2013 | Liverneaux et al. |
| 8,603,091 B2 | 12/2013 | Lutz |
| 8,608,783 B2 | 12/2013 | Graham |
| 8,690,916 B2 | 4/2014 | Gonzalez-Hernandez |
| 8,728,126 B2 | 5/2014 | Steffen |

(56) References Cited

U.S. PATENT DOCUMENTS

| | | |
|---|---|---|
| 8,764,808 B2 | 7/2014 | Gonzalez-Hernandez |
| 8,870,963 B2 | 10/2014 | Gonzalez-Hernandez |
| 8,906,070 B2 | 12/2014 | Medoff |
| 8,961,573 B2 | 2/2015 | Gonzalez-Hernandez |
| 2002/0091391 A1 | 7/2002 | Cole et al. |
| 2003/0135212 A1 | 7/2003 | Chow |
| 2003/0135216 A1 | 7/2003 | Sevrain |
| 2003/0208210 A1 | 11/2003 | Dreyfuss et al. |
| 2004/0097939 A1 | 5/2004 | Bonutti |
| 2004/0193278 A1 | 9/2004 | Maroney et al. |
| 2004/0199258 A1 | 10/2004 | Macara |
| 2004/0210220 A1 | 10/2004 | Tornier |
| 2005/0004574 A1 | 1/2005 | Muckter |
| 2005/0015089 A1 | 1/2005 | Young et al. |
| 2005/0021033 A1 | 1/2005 | Zeiler et al. |
| 2005/0038513 A1 | 2/2005 | Michelson |
| 2005/0085819 A1 | 4/2005 | Ellis et al. |
| 2005/0182405 A1 | 8/2005 | Orbay et al. |
| 2005/0240187 A1 | 10/2005 | Huebner et al. |
| 2005/0267476 A1 | 12/2005 | Chervitz et al. |
| 2005/0288681 A1 | 12/2005 | Klotz et al. |
| 2006/0015072 A1 | 1/2006 | Raulerson |
| 2006/0015101 A1 | 1/2006 | Warburton et al. |
| 2006/0058795 A1 | 3/2006 | Boyd |
| 2006/0106385 A1 | 5/2006 | Pennig |
| 2006/0161156 A1 | 7/2006 | Orbay |
| 2006/0217722 A1 | 9/2006 | Dutoit et al. |
| 2006/0229623 A1 | 10/2006 | Bonutti et al. |
| 2006/0235400 A1 | 10/2006 | Scheider |
| 2006/0241617 A1 | 10/2006 | Holloway et al. |
| 2006/0264947 A1 | 11/2006 | Orbay et al. |
| 2006/0264949 A1* | 11/2006 | Kohut ............... A61B 17/8061 606/71 |
| 2006/0264956 A1 | 11/2006 | Orbay et al. |
| 2006/0271105 A1 | 11/2006 | Foerster et al. |
| 2007/0005074 A1 | 1/2007 | Chudik |
| 2007/0016205 A1 | 1/2007 | Beutter et al. |
| 2007/0083207 A1 | 4/2007 | Ziolo et al. |
| 2007/0123880 A1 | 5/2007 | Medoff |
| 2007/0123885 A1 | 5/2007 | Kirschman |
| 2007/0162015 A1 | 7/2007 | Winquist et al. |
| 2007/0167953 A1 | 7/2007 | Prien et al. |
| 2007/0233113 A1 | 10/2007 | Kaelblein |
| 2007/0233114 A1 | 10/2007 | Bouman |
| 2007/0233115 A1 | 10/2007 | Sixto et al. |
| 2007/0265631 A1 | 11/2007 | Fox |
| 2008/0015593 A1 | 1/2008 | Pfefferle et al. |
| 2008/0045960 A1 | 2/2008 | Bruecker et al. |
| 2008/0119895 A1 | 5/2008 | Manceau |
| 2008/0132955 A1 | 6/2008 | Frigg |
| 2008/0140130 A1 | 6/2008 | Chan et al. |
| 2008/0154311 A1 | 6/2008 | Staeubli |
| 2008/0161853 A1 | 7/2008 | Arnold et al. |
| 2008/0161860 A1 | 7/2008 | Ahrens et al. |
| 2008/0161863 A1 | 7/2008 | Arnold et al. |
| 2008/0221577 A1 | 9/2008 | Elghazaly |
| 2008/0234749 A1 | 9/2008 | Forstein |
| 2008/0234752 A1 | 9/2008 | Dahners |
| 2008/0249572 A1 | 10/2008 | Tandon |
| 2009/0012571 A1 | 1/2009 | Perrow et al. |
| 2009/0024173 A1 | 1/2009 | Reis, Jr. |
| 2009/0048681 A1 | 2/2009 | Vlachos |
| 2009/0069851 A1 | 3/2009 | Gillard |
| 2009/0076554 A1 | 3/2009 | Huebner et al. |
| 2009/0105838 A1 | 4/2009 | Russo et al. |
| 2009/0118769 A1 | 5/2009 | Sixto, Jr. |
| 2009/0125070 A1 | 5/2009 | Sixto, Jr. et al. |
| 2009/0171399 A1 | 7/2009 | White et al. |
| 2009/0192550 A1 | 7/2009 | Leung et al. |
| 2009/0216270 A1 | 8/2009 | Humphrey |
| 2009/0228010 A1 | 9/2009 | Gonzalez-Hernandez et al. |
| 2009/0254089 A1 | 10/2009 | Tipirneni et al. |
| 2009/0254189 A1 | 10/2009 | Scheker |
| 2009/0264936 A1 | 10/2009 | Gonzalez-Hernandez et al. |
| 2009/0275987 A1 | 11/2009 | Graham et al. |
| 2009/0275991 A1 | 11/2009 | Medoff |
| 2009/0281577 A1 | 11/2009 | Graham et al. |
| 2009/0281578 A1 | 11/2009 | Spencer |
| 2009/0299369 A1 | 12/2009 | Orbay et al. |
| 2009/0306711 A1 | 12/2009 | Stone et al. |
| 2009/0312758 A1 | 12/2009 | Petit |
| 2009/0312760 A1 | 12/2009 | Forstein et al. |
| 2009/0312802 A1 | 12/2009 | Dasilva |
| 2009/0326591 A1 | 12/2009 | Spencer, Jr. |
| 2010/0030276 A1 | 2/2010 | Huebner et al. |
| 2010/0057086 A1 | 3/2010 | Price et al. |
| 2010/0094358 A1 | 4/2010 | Moore |
| 2010/0145339 A1 | 6/2010 | Steffen |
| 2010/0145397 A1 | 6/2010 | Overes et al. |
| 2010/0198258 A1 | 8/2010 | Heaven et al. |
| 2010/0217393 A1 | 8/2010 | Theofilos |
| 2010/0262194 A1 | 10/2010 | Wagner et al. |
| 2010/0324602 A1 | 12/2010 | Huebner et al. |
| 2010/0331844 A1 | 12/2010 | Ellis et al. |
| 2011/0066153 A1* | 3/2011 | Orbay ............... A61B 17/1739 606/71 |
| 2011/0152943 A1 | 6/2011 | Gonzalez-Hernandez |
| 2011/0160730 A1 | 6/2011 | Schonhardt et al. |
| 2011/0295324 A1 | 12/2011 | Donley |
| 2012/0226321 A1 | 9/2012 | Gonzalez-Hernandez |
| 2012/0226322 A1 | 9/2012 | Gonzalez-Hernandez |
| 2012/0226323 A1 | 9/2012 | Gonzalez-Hernandez |
| 2013/0096629 A1 | 4/2013 | Rollinghoff et al. |
| 2013/0116734 A1 | 5/2013 | Gonzalez-Hernandez |
| 2013/0338780 A1 | 12/2013 | Berchoux et al. |
| 2014/0121709 A1 | 5/2014 | Gonzalez-Hernandez |
| 2014/0121779 A1 | 5/2014 | Gonzalez-Hernandez |
| 2014/0172020 A1 | 6/2014 | Gonzalez-Hernandez |
| 2014/0180344 A1 | 6/2014 | Gonzalez-Hernandez |
| 2014/0277177 A1 | 9/2014 | Gonzalez-Hernandez |
| 2015/0164566 A1 | 6/2015 | Gonzalez-Hernandez |

FOREIGN PATENT DOCUMENTS

| | | |
|---|---|---|
| DE | 43 43 117 A1 | 6/1995 |
| DE | 198 57 279 A1 | 6/2000 |
| DE | 299 07 161 U1 | 8/2000 |
| EP | 0 551 588 A1 | 11/1992 |
| EP | 1 132 052 A2 | 9/2001 |
| EP | 1 468 655 A2 | 10/2004 |
| FR | 2 606 268 A1 | 5/1988 |
| FR | 2 680 673 A1 | 3/1993 |
| FR | 2 712 173 A1 | 5/1995 |
| JP | 4-138152 A | 5/1992 |
| WO | WO 99/38448 A1 | 8/1999 |
| WO | WO 02/071963 A1 | 9/2002 |
| WO | WO 2005/037117 A1 | 4/2005 |
| WO | WO 2008/007194 A2 | 1/2008 |
| WO | WO 2008/007196 A2 | 1/2008 |
| WO | WO 2012/003884 | 1/2012 |

OTHER PUBLICATIONS

ACUMED; The Mayo Clinic Congruent Elbow Plates (catalog); 2003; 19 pages.

ACUMED; The Mayo Clinic Congruent Elbow Plate System (catalog); Apr. 2006; 20 pages.

Christie, J., C.R. Howie and P.C. Armour, Fixation of displaced subcapital femoral fractures. Compression screw fixation versus double divergent pins. *J Bone Joint Surg [Br]* 1988; 70-B: 199-201.

Cross, W.M. et al., "Achieving stable fixation: biomechanical designs for fracture healing," AAOS Now (2008) 3 pages.

Guha, AR, et al.; "A New Technique of Fixation of Radial Head Fractures Using a Modified Tubular Plate," Journal of Postgraduate Medicine; Jul. 2004; vol. 50, Issue 2; pp. 113-114; Accessed Aug. 6, 2008 at: http://www.jpgmonline.com/article.asp?issn=0022-3859;year=2004;volume=50;issue=2;spage=113;epage=114;aulast=Guha.

Hand Innovations, LLC; DVR Anatomic, Volar Plating System; 2007; 4 pages.

Hussain M., R.N. Natarajan, A.H. Fayyazi, B.R. Braaksma, G.B. Andersson and H.S. An, *Screw angulation affects bone-screw stresses*

(56) References Cited

OTHER PUBLICATIONS

*and bone graft load sharing in an anterior cervical corpectomy fusion with a rigid screw-plate construct: a finite element model study*; Spine Journal, vol. 9, Issue 12; Dec. 2009; pp. 1016-1023 (published online Oct. 12, 2009).
Lakatos, R. et al.; "General principles of internal fixation"; eMedicine; Aug. 2006; 51 pages.
"MIS Technique," published by Zimmer®, 1 page, prior to Nov. 19, 2004.
Postak, Paul D.; "Biomechanical Properties of Fixed-Angle Volar Distal Radius Plates Under Dynamic Loading;" 2007; 6 pages.
Robert, III, K.Q., R. Chandler, R,V, Barratta, K.A. Thomas and M.B. Harris, The effect of divergent screw placement on the initial strength of plate-to-bone fixation. *J Trauma.* Dec. 2003;55(6):1139-44.
Synthes, "Large Fragment LCP Instrument and Implant Set;" technique guide; 2003; 31 pages.
Synthes; 3.5 mm LCP Periarticular Proximal Humerus Plate; Apr. 2010; 22 pages.
Synthes; Locking Compression Plate (LCP) System (brochure); 2003; 6 pages.
Synthes, "Locking Compression Plate (LCP) System. Locking screw technology and conventional plating in one system;" 2003; 6 pages.
Synthes; Locking Compression Plate (LCP) System (brochure); Jan. 2007; 6 pages.
Synthes; Modular Mini Fragment LCP System (brochure); 2007; 12 pages.
Synthes; Small Fragment Locking Compression Plate (LCP) System (brochure); 2002; 43 pages.
Written Opinion of the International Searching Authority; International Application No. PCT/US2009/036211; dated Sep. 23, 2010; 8 pages.
"Zimmer® Universal Locking System," The Journal of Bone and Joint Surgery, vol. 89, No. 7, Jul. 2007, 1 page.
Zimmer, Inc. "Zimmer® Universal Locking System," brochure (2006), 4 pages.
Zimmer, Inc.; "Zimmer Universal Locking System;" brochure; 2009, 2 pages.
Zimmer, Inc. "Zimmer Holdings to Launch Innovative Locking Plate System at Orthopaedic Trauma Association Meeting," Sep. 14, 2006; 3 pages.
Zimmer, Inc.; "Zimmer Small Fragment Universal Locking System;" Surgical Technique; 2010; 16 pages.
Zimmer; Zimmer Periarticular Plating System-Low-Profile Fixation (catalog); 2003; 8 pages.

* cited by examiner

SYSTEM AND METHOD FOR FRACTURE REPLACEMENT OF COMMINUTED BONE FRACTURES OR PORTIONS THEREOF ADJACENT BONE JOINTS

RELATED APPLICATIONS

This application is a divisional of U.S. application Ser. No. 14/522,702, filed Oct. 24, 2014; which is a divisional of U.S. application Ser. No. 13/282,810, filed Oct. 27, 2011 (U.S. Pat. No. 8,870,963); which claims the benefit of U.S. Provisional Application No. 61/407,072, filed Oct. 27, 2010, entitled "Proximal Humerus Hybrid Prosthesis Plate and Method of Use Associated Therewith"; all of which are incorporated by reference herein.

BACKGROUND

Field of the Invention

The present invention is generally related to a medical device and method for use thereof for facilitating replacement of comminuted bone fractures. In particular, the present invention is related to a system and method for use thereof to aid in the replacement of comminuted bone fractures adjacent bone joints to restore joint viability. More specifically, the present invention relates to a system and method for use thereof for replacing comminuted bone fractures adjacent joints by providing a prosthesis to replace the fractured bone to facilitate restoration of movement associated with the bone joint.

Description of the Prior Art

Comminuted bone fractures adjacent joints oftentimes result in significant fragmentation of the bone. In fact, these types of bone fractures can often result in portions of the bone being severely fragmented. That is, the number of fragments created by these types of bone fractures pose difficulties in repairing the bone. Bone plates have oftentimes been used to aid repair of the comminuted bone fractures. However, even with use of bone plates, the comminuted bone fractures may not be adequately reconstructed. For example, if severely fragmented, the proximal and distal end portions of a humerus may not be reconstructible. As such, there is a need for a prosthesis affording replacement of the comminuted bone fractures or portions thereof to restore joint viability. The prosthesis can be used when the comminuted bone fractures need substantial support to aid repair or are irretrievably fragmented. Such a prosthesis, for example, can be configured to repair the proximal and distal ends of the humerus.

SUMMARY OF THE INVENTION

The present invention in one embodiment contemplates a method for replacing at least a portion of a comminuted humeral head, the method including the following acts. A prosthesis is provided that has an exterior portion having an exterior surface, and an interior portion having at least one aperture formed therein, the exterior surface approximating the surface of the at least a portion of the comminuted humeral head in size and shape, and the at least one aperture of the prosthesis being configured to receive at least one fastener therein. A bone plate is provided that has at least one opening formed therein, the at least one aperture of the bone plate being configured to receive the at least one fastener therethrough. At least a portion of the comminuted humeral head is removed. The bone plate is attached to at least a portion of a humerus. The at least one aperture of the prosthesis is aligned with the at least one opening of the bone plate. The at least one fastener is inserted through the at least one opening and into the at least one aperture. The prosthesis and the bone plate are securely attached to one another across the humerus using the fastener.

In another preferred embodiment, the present invention contemplates a system for replacement of at least a portion of a comminuted humeral head. The system includes a prosthesis, a bone plate, and at least one fastener. The prosthesis has an exterior portion having an exterior surface and an interior portion having at least one aperture formed therein, the exterior surface being sized and shaped to approximate the surface of the at least a portion of the comminuted humeral head, and the at least one aperture of the prosthesis configured to receive at least one fastener therein. The bone plate including at least one opening formed therein, the at least one opening of the bone plate being configured to receive the at least one fastener therethrough. The at least one fastener having a first end for insertion through the at least one opening and into the at least one aperture, the at least one fastener being configured to secure attachment of the prosthesis and the bone plate to one another across a portion of a humerus.

In yet another preferred embodiment, the present invention contemplates a method for replacing at least a portion of a fractured capitellum and/or a fractured trochlea, the method including the following acts. An apparatus is provided that has a prosthesis portion and a plate portion, the prosthesis portion having an exterior surface, and the plate portion including a first leg portion extending outwardly from the prosthesis portion and a second leg portion extending outwardly from the prosthesis portion. At least a portion of the fractured capitellum and/or the fractured trochlea is removed. The prosthesis portion is sized and shaped according to the portion of the fractured capitellum and/or the fractured trochlea removed, the prosthesis portion having an exterior surface approximating the exterior surface of the removed portion of the fractured capitellum and/or the fractured trochlea. The prosthesis portion is positioned relative to the humerus. The first leg portion is attached to the lateral column of the humerus and the second leg portion is attached to the medial column of the humerus.

It is understood that both the foregoing general description and the following detailed description are exemplary and exemplary only, and are not restrictive of the invention as claimed.

BRIEF DESCRIPTION OF THE DRAWINGS

The accompanying drawings, which are incorporated in and constitute a part of the specification, illustrate preferred embodiments of the invention. Together with the description, they serve to explain the objects, advantages and principles of the invention. In the drawings.

DETAILED DESCRIPTION OF THE PREFERRED EMBODIMENT

The systems for fracture replacement of comminuted bone fractures or portions thereof and the method for use of the system are depicted in the accompanying drawings. The systems of the present invention provide a prosthesis affording replacement of the comminuted bone fractures or portions thereof. While the below-described systems are used in association with the proximal and distal end portions of a humerus, the present invention is not limited thereto. That is, the system and method of the present invention can be configured for use elsewhere in the human body.

Figure 1:
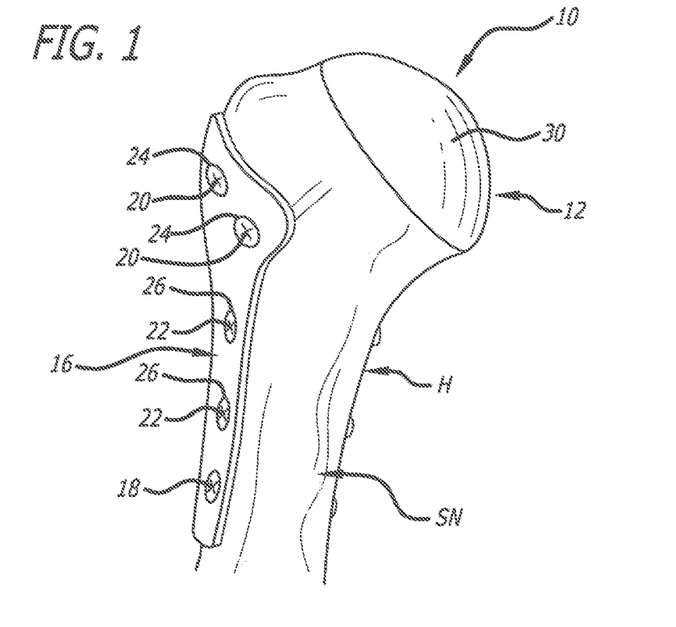
FIG. 1 is a perspective view of a first embodiment of a system for fracture repair and/or replacement for use with and depicted as attached to a proximal portion of a humerus.
Figure 2:
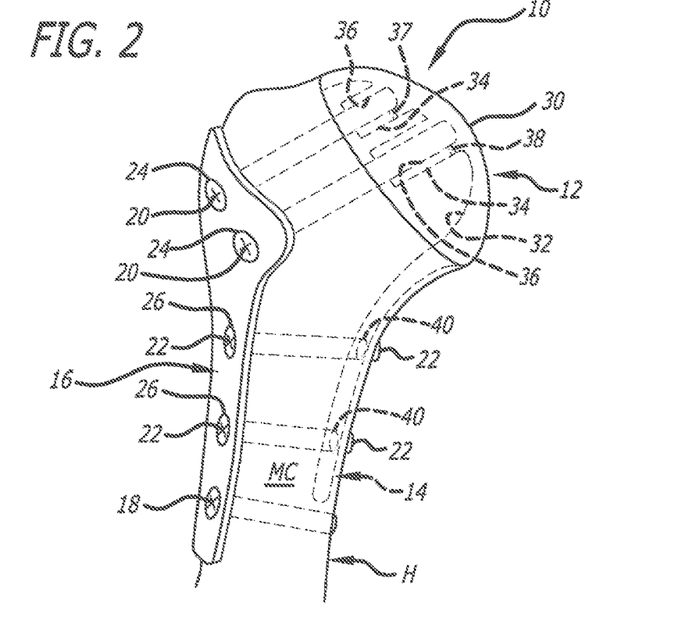
FIG. 2 is the perspective view of FIG. 1 showing a humeral head prosthesis, an extension portion, and fasteners of the first embodiment of the system in phantom with respect to the humerus.

A first illustrative embodiment of the system is generally indicated by the numeral 10 in FIGS. 1 and 2, and a second illustrative embodiment of the system is generally indicated by the numeral 100 in FIGS. 3-6A. First system 10 is used in replacing a fractured humeral head or portions thereof at the proximal end of the humerus and second system 100 is used in replacing a fractured capitellum and/or a fractured trochlea or portions thereof at the distal end of the humerus. In doing so, first and second systems 10 and 100 serve to repair the proximal and distal ends, respectively, of the humerus, and serve in restoring joint viability. The components of each of systems 10 and 100 are constructed of metal or other artificial material suitable for human implantation.

First system 10 is provided to facilitate replacement of a humeral head or portions thereof (not shown) at the proximal end of a humerus H (FIGS. 1 and 2) that have been irretrievably fragmented. Furthermore, while first system 10 is depicted replacing the humeral head or portion thereof, first system 10, for example, could be configured for replacing portions of a distal ulna. First system 10 includes a head portion 12 (or prosthetic portion), an optional extension portion 14 (of the medial calcar), and a bone plate 16. Head portion 12 serves as prosthesis for replacement of the humeral head or portions thereof, and bone plate 16 is configured to provided a rigid structure for attaching head portion 12 and extension portion 14 thereto. Extension portion 14 provides additional structural integrity, but, depending on the needs of the patient, may not be necessary.

Bone plate 16 is attached to surgical neck SN of humerus H. Bone plate 16 is configured to receive one or more bone screws 18 therethrough for attachment to surgical neck SN. Bone screws 18 are exclusively used for attachment of bone plate 16 to surgical neck SN.

Bone plate 16 also is configured to receive fasteners (such as bolts, posts, and/or screws) 20 and 22 for engagement with head portion 12 and extension portion 14, respectively. If fasteners 20 and 22 are bolts and/or screws, then fasteners 20 and 22 could threadably engage head portion 12 and extension portion 14, respectively, to facilitate attachment. Furthermore, if fasteners 20 and 22 are posts, then fasteners 20 and 22 could be attached to head portion 12 and extension portion 14, respectively, using interference fits therebetween. Thus, whether fasteners 20 and 22 are bolts, posts, and/or screws, the fasteners, and head portion 12 and extension portion 14 would include complementary structures facilitating attachment.

To facilitate engagement of bone plate 16 with head portion 12 and extension portion 14 using fasteners 20 and 22, respectively, bone plate 16 includes openings 24 and 26 therethrough. Openings 24 are provided at or adjacent the upper portion of bone plate 16 for receiving fasteners 20, and openings 26 are provided at or adjacent the middle portion of bone plate 16 for receiving fasteners 22. After insertion thereof through bone plate 16, fasteners 20 and 22 engage head portion 12 and extension portion 14, respectively, to provide for the rigid attachment of humeral head prosthesis 10 to humerus H. In addition to threads (not shown) or structures (not shown) for providing for an interference fit to facilitate engagement with head portion 12 and extension portion 14, fasteners 20 and 22 can include threads (not shown) for engaging complementary threads (not shown) provided in openings 24 and 26 to lock fasteners 20 and 22 to bone plate 16. Moreover, fasteners 20 and 22 could include threads facilitating attachment to portions of humerus H that fasteners 20 and 22 extend through.

Head portion 12 can be sized and shaped according to the portions of the humeral head being replaced. As such, portions of head portion 12 serve in reproducing the articular surface of the proximal humerus that is being replaced using system 10. Thus, if only a portion of the humeral head requires replacement, head portion 12 can be sized and shaped to approximate the size and shape of the portion of the humeral head being replaced. However, if the entirety of the humeral head is being replaced, head portion 12 can be sized and shaped to approximate the size and shape of the entirety of the humeral head. As depicted in FIGS. 1 and 2, head portion 12 is sized and shaped to replace the entirety of the humeral head.

Head portion 12 includes an exterior-facing portion having an exterior surface 30, and an interior-facing portion of having an interior surface 32, columns 34, and apertures 36 for receiving fasteners 20 therein. Apertures 36 can include complementary threads (not shown) or structures (not shown) for providing an interference fit to facilitate engagement with fasteners 20. As depicted in FIGS. 1 and 2, exterior surface 30 is convex and is configured to mimic the shape of the humeral head or portions thereof to reproduce the articular surface of the proximal humerus being replaced. Accordingly, portions of exterior surface 30 can be highly polished or lubricated. Furthermore, as depicted in FIG. 2, interior surface 32 is concave, and columns 34 extend outwardly from interior surface 32.

Columns 34 include apertures 36 for receiving fasteners 20 therein. However, the present invention is not limited to using columns 34. For example, if interior surface 32 is flattened (rather than concave) and an adequate depth of material is provided between exterior surface 30 and interior surface 32, apertures 36 could be formed through interior surface 32 into the material provided between exterior surface 30 and interior surface 32.

Furthermore, relief holes 38 are provided through columns 34 to communicate with apertures 36. Relief holes 38 allow tissues, fluids, and/or air that were present in apertures 36 (prior to insertion of fasteners 20 therein) to be expelled therefrom as fasteners 20 are tightened in position.

While head portion 12 is depicted in FIGS. 1 and 2 as being a single integral component, head portion 12 can be composed of two or more elements that can be integrated with one another during implantation of system 10. For example, head portion 12 could be composed of a base plate (not shown) and a portion (not shown) including exterior surface 30. The base plate would first be attached to bone plate 16 using fasteners 20, and then the portion including exterior surface 30 would be attached to the base plate. The base plate and the portion including exterior surface 30 could include a complementary attachment mechanism shared therebetween to facilitate integration thereof. As such, a standard sized and shaped base plate could be utilized, and only the portion including exterior surface 30 would be sized and shaped according to the portions of the humeral head being replaced.

Extension portion 14, as depicted in FIG. 2, depends downwardly from head portion 12. Extension portion 14 is inserted into medullary cavity MC, and is configured to interface with the bone adjacent medullary cavity MC. Furthermore, using fasteners 22, extension portion 14 can be attached to the medial cortex of humerus H. To that end, extension portion 14 includes apertures 40 for receiving fasteners 22. Like apertures 36 of head portion 12, apertures 40 can also include complementary threads (not shown) or structures (not shown) for providing an interference fit to facilitate engagement with fasteners 22.

Rather than or in addition to using fasteners 20 and 22, integral posts (not shown) formed with bone plate 16 could be used to attach bone plate 16 with head portion 12 and/or extension portion 14. For example, an integral post that extends outwardly from bone plate 16 could be positioned adjacent apertures 24. Furthermore, a portion of the integral post could be received in one of apertures 36, and the integral post and the one of apertures 36 could include complementary structures (not shown) facilitating attachment therebetween.

Moreover, while fasteners 20 and 22 are shown as being inserted through bone plate 16 and into head portion 12 and extension portion 14, respectively, head portion 12, extension portion 14, and bone plate 16 could be configured to provide the opposite arrangement—fasteners 20 and 22 could be inserted through head portion 12 and extension portion 14, respectively, and into bone plate 16. As such, head portion 12, extension portion 14, and bone plate 16 would include complementary configurations to afford such an arrangement. For example, head portion 12 could include an opening (not shown) extending through the exterior-facing portion and the interior-facing portion thereof. Thus, a fastener (similar, if not identical, to fastener 20) could be inserted through such an opening and into a corresponding aperture formed in bone plate 16.

To secure attachment of first system 10 to humerus H using the configuration thereof depicted in FIGS. 1 and 2, the fractured humeral head or portions thereof are removed from adjacent humerus H. Bone plate 16 is initially attached to surgical neck SN using bone screw 18. Thereafter, openings 24 and 26 through bone plate 16 can be used as drill guides for receiving a drill to create alignment holes through humerus H. The alignment holes created by the drill will ultimately afford alignment between holes 24 in bone plate 16 and apertures 36 in head portion 12, and between holes 26 in bone plate 16 and apertures 40 in extension portion 14. Once the alignment holes are created, head portion 12 is positioned with respect to humerus H. Fasteners 20 and 22 are then inserted through openings 24 and 26 into apertures 36 and 49, respectively. Tightening of fasteners 20 and 22 in holes 36 and 40 serve to secure engagement of head portion 12 to humerus 10. As such, head portion 12, extension portion 14, and bone plate 16 and fasteners 20 and 22 extending therebetween provide an effective structural lattice allowing head portion 12 to provide an effective replacement for the humeral head or portions thereof that are severely fractured. Via replacement of the humeral head or portions thereof using first system 10, the viability of the shoulder joint adjacent to head portion 12 can be restored.

As discussed above, second system 100 is provided to facilitate replacement of a fractured capitellum and/or a fractured trochlea or portions thereof (not shown) at the distal end of the humerus. As depicted in FIGS. 3-6A, second system 100 includes a prosthetic portion 102 and a plate portion 104. Prosthetic portion 102 and plate portion 104 are depicted in FIGS. 3-6A as being formed integrally with one another. However, second system 100 is not limited thereto. Prosthetic portion 102 and plate portion 104 can be formed separately from one another and then cooperatively engaged to (or integrated with) one another. For example, prosthetic portion 102 and plate portion 104 could be fastened to one another using a fastener extending through portions thereof during implantation of system 100. Furthermore, while second system 100 is configured to replace the fractured capitellum and/or the fractured trochlea or portions thereof, second system 100 is not limited thereto. For example, second system 100 also could be configured to replace fractured portions of the humerus such as the lateral epicondyle, the olecranon fossa, and/or medial epicondyle.

Prosthetic portion 102 serves as a prosthesis for replacement of the fractured capitellum and/or the fractured trochlea or portions thereof. As such, prosthetic portion 102 could be shaped to replace the entirety of both of the fractured capitellum and the fractured trochlea, or various portions of the fractured capitellum and/or the fractured trochlea. Furthermore, plate portion 104 is configured to provide a rigid structure for attaching prosthetic portion 102 to the humerus.

Figure 3:
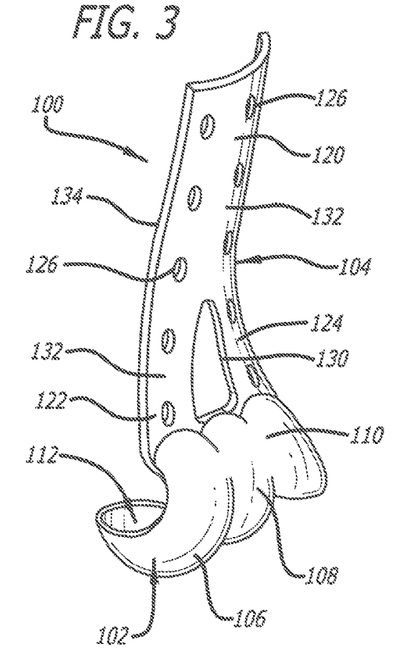
FIG. 3 is a perspective view of a second embodiment of the system for fracture repair and/or replacement for use with a distal portion of the humerus.
Figure 4:
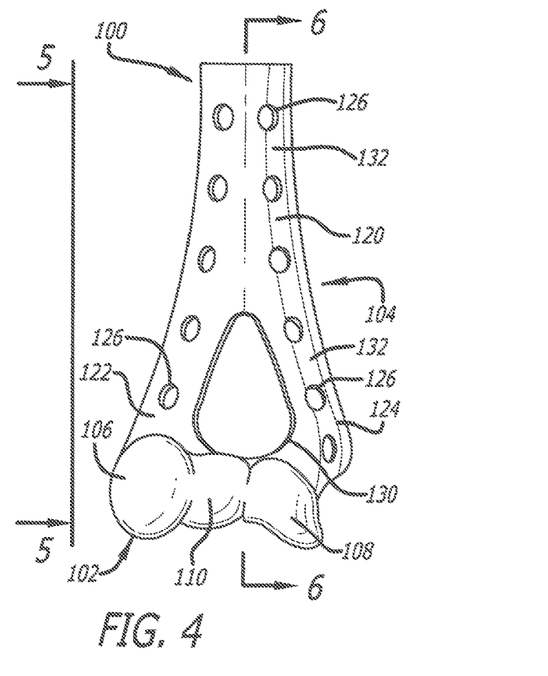
FIG. 4 is a front elevational view of the second embodiment of the system depicted in FIG. 3.
Figure 5:
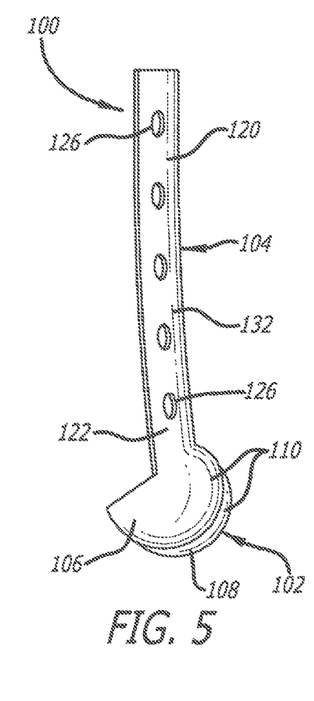
FIG. 5 is a side elevational view of the second embodiment of the system depicted in FIGS. 3 and 4.

As depicted in FIGS. 3-5, prosthetic portion 102 includes a capitellum portion 106 and a trochlea portion 108. As discussed above, the entirety of the fractured capitellum and/or the fractured trochlea or portions thereof can be replaced using prosthetic portion 102. Thus, prosthetic portion 102 includes an exterior surface 110 (extending over capitellum portion 106 and trochlea portion 108) that can be sized and shaped according to the portions of the fractured capitellum and/or the fractured trochlea requiring replacement. As such, portions of prosthetic portion 102 serve in reproducing the articular surface of the distal humerus that is being replaced using system 100. Accordingly, portions of exterior surface 110 can be highly polished or lubricated.

For example, if only the entirety of fractured capitellum requires replacement, then prosthetic portion 102 (and exterior surface 110 thereof) would be sized and shaped to approximate the entirety of the capitellum and could incorporate only capitellum portion 106. Furthermore, if only the entirety of the fractured trochlea requires replacement, prosthetic portion 102 (and exterior surface 110 thereof) would be sized and shaped to approximate the entirety of the trochlea and could incorporate only trochlea portion 108. However, if only selected portions of the fractured capitellum and the fractured trochlea require replacement, then prosthetic portion 102 (and exterior surface 110 thereof) would be sized and shaped to approximate the selected portions by incorporating corresponding portions of capitellum portion 106 and trochlea portion 108.

Figure 6:
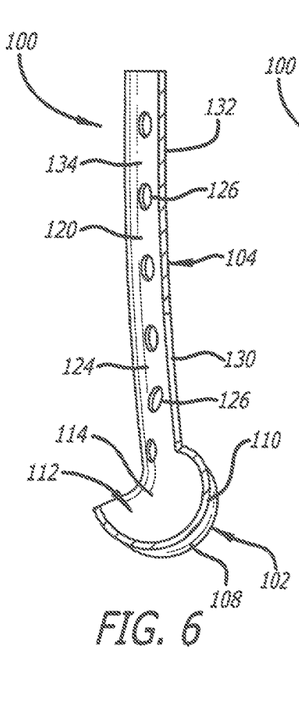
FIG. 6 is a cross-sectional view of the second embodiment of the system depicted in FIGS. 3-5 taken along Line 6-6 of FIG. 4.
Figure 6A:
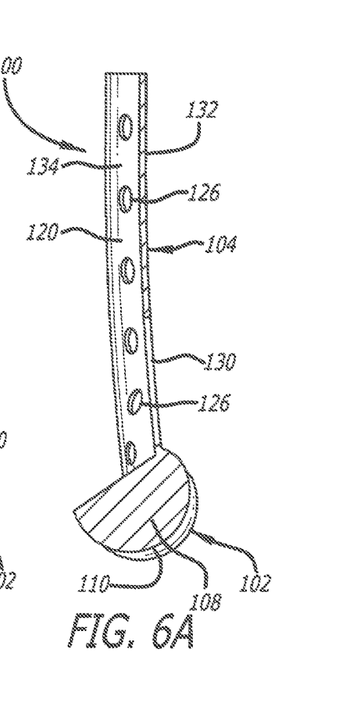
FIG. 6A is a alternative cross section for the second embodiment of the system depicted in FIGS. 3-6.

Furthermore, prosthetic portion 102 can be constructed to be hollow to include a cavity 112. As depicted in FIGS. 3 and 6, cavity 112 is formed behind exterior surface 110, and thus, an interior surface 114 (of cavity 112) is opposite exterior surface 110. Cavity 112 can be filled with bone graft materials, and/or portions of the fractured capitellum and the fractured trochlea that the prosthetic portion 102 is being used to replace. Alternatively, prosthetic portion 102 can be constructed of solid material as depicted in the cross-sectional view of FIG. 6A. As such, prosthetic portion 102 would be formed of solid material approximating the portions of the fractured capitellum and/or the fractured trochlea being replaced.

As depicted in FIGS. 3 and 4, plate portion 104 extends outwardly from prosthetic portion 102, and includes a body portion 120, a first leg portion 122, and a second leg portion 124. First leg portion 122 extends outwardly from capitellum portion 106, and second leg portion 124 extends outwardly from trochlea portion 108. Furthermore, first and second leg portions 122 and 124 extend from prosthetic portion 102 to terminate at body portion 120.

An aperture 130, as depicted in FIGS. 3 and 4 is formed between prosthesis portion 102 and first and second leg portions 122 and 124. Furthermore, plate portion 104 includes a front surface 132 and a rear surface 134 opposite the front surface 132. As discussed below, portions of rear surface 134 (which encompasses body portion 120, first leg portion 122, and second leg portion 124) is engaged to portions of the humerus. As such, rear surface 134 can be at least in part concave (FIG. 6) to facilitate such engagement.

Body portion 120 is attached to the shaft (not shown) of the humerus. Furthermore, first leg portion and second leg portions 122 and 124 are attached to the humerus—first leg portion 120 is attached to the lateral column (not shown) and second leg portion 122 is attached to the medial column (not shown). To that end, body portion 120, first leg portion 122, and second leg portion 124 can include various apertures 126. Apertures 126 can be configured to receive bone screws (not shown) therethrough to attach plate portion 104 to the humerus.

In addition to threads (not shown) for engaging the humerus, the bone screws used to attach the plate portion thereto can include threads (not shown) for engaging complementary threads (not shown) provided in apertures 126 to lock the bone screws to plate portion 104. Furthermore, if necessary, a second plate portion (not shown) can be positioned on the opposite side of the humerus of plate portion 104 to afford another attachment structure for plate portion 104. Thus, additional fasteners (such as bolts and/or screws) could be used to interconnect plate portion 104 and the second plate portion to further enhance the rigidity of the structure attaching prosthetic portion 102 to the humerus.

To secure attachment of the first system 100 to the humerus, the fractured capitellum and/or the fractured trochlea or portions thereof are removed from adjacent the humerus. Thereafter, plate portion 104 is attached to the humerus with or without drilling into the humerus. If holes are drilled in the humerus to receive the bone screws, apertures 126 through plate portion 104 can be used as drill guides for receiving a drill. The bone screws are thereafter inserted through apertures 126 and into the humerus. Using the bone screws to facilitate attachment to the humerus, body portion 120 is attached to the shaft, first leg portion 120 is attached to the lateral column, and second leg portion 122 is attached to the medial column. The attachment of body portion 120, first leg portion 122, and second leg portion 124 to the humerus provides the structural rigidity necessary to allow prosthetic portion 102 to provide an effective replacement for the fractured capitellum and/or the fractured trochlea or portions thereof. Via replacement of the fractured capitellum and/or the fractured trochlea or portions thereof using second system 100, the viability of the elbow joint adjacent to prosthesis portion 102 can be restored.

In summary, systems 10 and 100 for replacement of comminuted bone portions and the method for use thereof provide a prosthesis affording replacement of the comminuted bone fractures or portions thereof. Furthermore, while systems 10 and 100 are used in association with the proximal and distal end portions, respectively, of the humerus, the system and method of the present invention can be configured for use elsewhere in the human body. Other embodiments of the invention will be apparent to those skilled in the art from consideration of the specification and practice of the invention disclosed herein. Accordingly, it is intended that the specification and examples be considered as exemplary only.

What is claimed is:

1. A method for replacing at least a portion of a fractured capitellum and/or a fractured trochlea of a humerus of an elbow joint, the method comprising the acts of:

providing an apparatus having a first end, an opposite second end, a prosthesis portion at and adjacent the first end, and a plate portion extending from the prosthesis portion toward the second end, the prosthesis portion having an exterior surface;

removing at least a portion of the fractured capitellum and/or the fractured trochlea;

sizing and shaping an exterior surface of the prosthesis portion to reproduce the removed portion of the fractured capitellum and/or the fractured trochlea, the exterior surface of the prosthesis portion replicating at least a portion of an articular surface of the elbow joint;

positioning the prosthesis portion relative to the humerus; and attaching at least a portion of the plate portion to the humerus.

2. The method of claim 1, further comprising providing the plate portion with a first leg portion, a second leg portion, and a body portion, the body portion connecting portions of the first leg portion and the second leg portion to one another, and the body portion extending from the first leg portion and the second leg portion to the second end of the apparatus.

3. The method of claim 2, further comprising attaching the body portion to the shaft of the humerus.

4. The method of claim 2, wherein the first leg portion and the second portion are spaced apart from one another between the prosthesis portion and the body portion.

5. The method of claim 2, wherein each of the first leg portion, the second leg portion, and the body portion include apertures for facilitating attachment of the plate portion to bone.

6. The method of claim 2, wherein the body portion includes a first surface and an opposite second surface, at least a portion of the first surface being concave, and further comprising contacting the first surface to the humerus, and attaching the body portion to the humerus.

7. The method of claim 1, wherein the prosthesis portion includes an interior surface opposite the exterior surface, the interior surface forming a cavity, and the cavity being adapted to receive bone graft materials.

8. The method of claim 7, wherein sizing and shaping of the prosthesis portion reproduces the removed portions of both of the fractured capitellum and the fractured trochlea.

9. A method for replacing at least a portion of a fractured capitellum and/or a fractured trochlea of a humerus of an elbow joint, the method comprising the acts of:

providing an apparatus having a prosthesis portion and a plate portion, the prosthesis portion having an exterior surface, and the plate portion including a first leg portion extending outwardly from the prosthesis portion and a second leg portion extending outwardly from the prosthesis portion;

removing at least a portion of the fractured capitellum and/or the fractured trochlea;

sizing and shaping an exterior surface of the prosthesis portion to reproduce the removed portion of the fractured capitellum and/or the fractured trochlea, the exterior surface of the prosthesis portion replicating at least a portion of an articular surface of the elbow joint;

positioning the prosthesis portion relative to the humerus; and attaching the first leg portion to a lateral column of the humerus and the second leg portion to a medial column of the humerus.

10. The method of claim 9, further comprising providing the plate portion with a body portion, the body portion connecting portions of the first leg portion and the second leg portion to one another.

11. The method of claim 10, further comprising attaching the body portion to the shaft of the humerus.

12. The method of claim 9, wherein the prosthesis portion includes an interior surface opposite the exterior surface, the interior surface forming a cavity, and the cavity being adapted to receive bone graft materials.

13. The method of claim 12, wherein sizing and shaping of the prosthesis portion reproduces the removed portions of both of the fractured capitellum and the fractured trochlea.

14. The method of claim 10, wherein the first leg portion and the second portion are spaced apart from one another between the prosthesis portion and the body portion.

15. The method of claim 10, wherein each of the first leg portion, the second leg portion, and the body portion include apertures for facilitating attachment of the plate portion to bone.

16. The method of claim 10, wherein the body portion includes a first surface and an opposite second surface, at least a portion of the first surface being concave, and further comprising contacting the first surface to the humerus, and attaching the body portion to the humerus.

* * * * *